United States Patent
Aono

(10) Patent No.: US 9,915,634 B2
(45) Date of Patent: Mar. 13, 2018

(54) HEAD SPACE SAMPLE INTRODUCTION DEVICE AND GAS CHROMATOGRAPH INCLUDING SAME

(75) Inventor: Akira Aono, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 193 days.

(21) Appl. No.: 14/422,928

(22) PCT Filed: Sep. 5, 2012

(86) PCT No.: PCT/JP2012/072635
§ 371 (c)(1),
(2), (4) Date: Feb. 20, 2015

(87) PCT Pub. No.: WO2014/038019
PCT Pub. Date: Mar. 13, 2014

(65) Prior Publication Data
US 2015/0233874 A1 Aug. 20, 2015

(51) Int. Cl.
*G01N 30/16* (2006.01)
*G01N 1/22* (2006.01)
*G01N 30/02* (2006.01)

(52) U.S. Cl.
CPC .............. *G01N 30/16* (2013.01); *G01N 1/22* (2013.01); *G01N 2030/025* (2013.01)

(58) Field of Classification Search
CPC ..... G01N 30/16; G01N 1/22; G01N 2030/025
USPC ........... 73/23.41; 422/89, 70; 210/98.2, 656; 436/161; 95/82; 96/101
See application file for complete search history.

(56) References Cited

U.S. PATENT DOCUMENTS

| 6,834,531 B2 * | 12/2004 | Rust ..................... F27D 11/00 219/385 |
| 8,794,052 B2 * | 8/2014 | Maeda .................. G01N 30/20 73/61.55 |
| 2010/0107730 A1 * | 5/2010 | Aono ..................... G01N 30/12 73/23.39 |

FOREIGN PATENT DOCUMENTS

| JP | 9-101292 A | 4/1997 |
| JP | 2001-165918 A | 6/2001 |
| JP | 3159793 U | 6/2010 |

OTHER PUBLICATIONS

International Search Report dated Nov. 13, 2012 issued in corresponding application No. PCT/JP2012/072635.
Office Action dated Feb. 4, 2017, issued in counterpart Chinese Application No. 201280075395.0, with English translation. (8 pages).

* cited by examiner

Primary Examiner — Natalie Huls
Assistant Examiner — Monica S Young
(74) Attorney, Agent, or Firm — Westerman, Hattori, Daniels & Adrian, LLP

(57) ABSTRACT

A pressurization passage that divides a constant pressure from a pressure source with passage resistances so as to have a predetermined constant pressure is disposed on a downstream side of a sample loop in order to maintain a back pressure of the sample loop constant when a sample gas is collected to the sample loop.

8 Claims, 8 Drawing Sheets

HEAD SPACE SAMPLE INTRODUCTION DEVICE AND GAS CHROMATOGRAPH INCLUDING SAME

TECHNICAL FIELD

The present invention relates to a head space sample introduction device that collects a gaseous sample volatilized from a liquid sample or a solid sample by a head space method and introduces the gaseous sample into an analyzer, such as a gas chromatograph, and relates to a gas chromatograph as one example of an analyzer including the head space sample introduction device.

BACKGROUND ART

A head space method is a sample introduction method for heating a liquid sample or a solid sample stored in a sample container at a predetermined temperature for a predetermined period of time to volatilize components having relatively low boiling points, collecting a predetermined amount of gas containing these components from a head space (upper space) in the sample container, and introducing the gas into an analyzer. Further, a head space analysis method is a method for introducing a sample into an analyzer by the head space method to analyze the sample. A typical example of the analyzer that performs such a head space analysis method includes a gas chromatograph.

The head space method includes collecting the sample gas from the head space of the sample container to a sample loop, and introducing the collected sample gas into the analyzer. As a method for collecting the sample gas to the sample loop, the sample gas is generally collected to the sample loop when a pressure at one end of the sample loop becomes atmospheric pressure, the other end of the sample loop being connected to the head space of the sample container. However, when an inside of the sample loop is in the atmospheric pressure state, a sample component concentration may decrease, and analysis sensitivity may be insufficient.

The sample gas can be collected to the sample loop by switching a valve when the pressure inside the sample loop is a predetermined pressure before decreasing to the atmospheric pressure. In such a case, however, valve switching operation is necessary while predicting time at which the pressure inside the sample loop becomes the predetermined pressure in a state where the pressure changes with time. In addition, reproducibility of a measuring result lowers because a concentration of the collected sample gas fluctuates depending on the switching timing in such a method for switching the valve when the pressure changes.

A pressure sensor and a flow rate regulating valve, therefore, a have been provided on one end side of the sample loop having the other end connected to the head space of the sample container, and feedback control of the flow rate regulating valve has been performed by output of the pressure sensor in such a way that a back pressure on one end side of the sample loop when the sample gas is collected to the sample loop becomes a predetermined constant pressure larger than atmospheric pressure.

DISCLOSURE OF THE INVENTION

Problem to be Solved by the Invention

In the method for performing the feedback control of the flow rate regulating valve in order to make the back pressure of the sample loop become constant when the sample gas is collected to the sample loop, a feedback control device including the flow rate regulating valve is necessary, and results in a high cost. Further, there is a problem that a head space gas containing volatilized sample components flows through the flow rate regulating valve, and thus, the flow rate regulating valve is contaminated due to the sample components to be deteriorated, thus lowering reliability of the feedback control.

An object of the present invention is to make a back pressure of a sample loop become constant when a sample gas is collected to the sample loop with a simple configuration without using a flow rate regulating valve.

Means for Solving the Problem

In the present invention, a pressurization passage that divides a constant pressure from a pressure source with passage resistances so as to have a predetermined constant pressure is provided on a downstream side of a sample loop in order to make a back pressure of the sample loop become constant when a sample gas is collected to the sample loop.

A head space sample introduction device of the present invention includes a sample gas passage that connects to a head space of a sample container, the head space for storing a sample gas generated from a sample; a first pressurization passage that is connected to a pressurization gas supply source of a constant first pressure larger than atmospheric pressure; a sample loop that collects the sample gas; a discharge passage that discharges the sample gas; a carrier gas passage to which a carrier gas is supplied; an analysis passage that is connected to an analyzer; a second pressurization passage that applies a constant pressure larger than atmospheric pressure to the discharge passage; and a passage switching mechanism. The passage switching mechanism is configured to switch among a head space pressurization passage configuration in which the first pressurization passage is connected to the head space, a sample gas collection passage configuration in which the sample loop is connected between the sample gas passage and the discharge passage, and a sample gas introduction passage configuration in which the sample loop is connected between the carrier gas passage and the analysis passage.

Further, in order to apply the constant pressure larger than the atmospheric pressure to the discharge passage without performing feedback control, the second pressurization passage includes a first resistance pipe having one end connected to a downstream side of the discharge passage and the other end exposed to the atmosphere, and a second resistance pipe having one end connected to the downstream side of the discharge passage and the other end connected to a pressurization gas supply source of a constant second pressure larger than atmospheric pressure, and the second pressurization passage applies to the discharge passage the constant pressure larger than atmospheric pressure obtained by dividing the second pressure with the first and second resistance pipes.

The pressurization gas supply source to which the first pressurization passage is connected, and the pressurization gas supply source to which the second pressurization passage is connected can be different from or common to each other. Part of the gas supplied from the first pressurization passage to the sample container in order to increase the pressure of the head space of the sample container is collected into the sample loop together with the sample gas and then introduced into the analyzer together with the carrier gas. Therefore, the gas supplied from the first pressurization passage is desired to be the same as the carrier gas. Meanwhile, the pressurization gas used in the second pressurization passage is not introduced into the analyzer, and thus, is not necessarily the same as the carrier gas.

In the case where the pressurization gas supply source to which the first pressurization passage is connected, and the pressurization gas supply source to which the second pressurization passage is connected are different from each other, the pressurization gas supply source to which the second pressurization passage is connected can use a gas cheaper than the carrier gas, such as air, or nitrogen, as the pressurization gas, thus suppressing consumption of the expensive carrier gas.

Meanwhile, in the case where the pressurization gas supply source to which the first pressurization passage is connected, and the pressurization gas supply source to which the second pressurization passage is connected are common to each other, a configuration of the pressurization gas supply source becomes simple even though the consumption of the carrier gas increases.

The analyzer using the head space sample introduction device of the present invention is not particularly limited as long as the analyzer analyzes the collected sample gas, but a typical example thereof is a gas chromatograph. A gas chromatograph of the present invention includes a gas chromatograph main body including a separation column to which the sample gas is supplied together with the carrier gas, and a detector that detects a sample component separated with the separation column; and the head space sample introduction device of the present invention. Further, the analysis passage of the head space sample introduction device is connected to the separation column of the gas chromatograph main body.

In the gas chromatograph of one embodiment, the pressurization gas supply source to which the first pressurization passage is connected is configured to supply a gas identical with the carrier gas supplied from the carrier gas passage as the pressurization gas.

In the gas chromatograph of one embodiment, the pressurization gas supply source to which the first pressurization passage is connected, and the pressurization gas supply source to which the second pressurization passage is connected are common to each other, so that the pressurization gas supply source can supply the gas identical with the carrier gas supplied from the carrier gas passage as the pressurization gas.

In the gas chromatograph of another embodiment, the pressurization gas supply source to which the first pressurization passage is connected, and the pressurization gas supply source to which the second pressurization passage is connected are different from each other, and the pressurization gas supply source to which the first pressurization passage is connected can supply the gas identical with the carrier gas supplied from the carrier gas passage as the pressurization gas, and the pressurization gas supply source to which the second pressurization passage is connected can supply a gas other than the carrier gas.

Effect of the Invention

In the present invention, a pressurization passage that divides a constant pressure from a pressure source with passage resistances so as to have a predetermined constant pressure is provided on a downstream side of a sample loop, and therefore, a configuration for making a back pressure of the sample loop become constant when a sample gas is collected to the sample loop becomes simple. Further, a feedback control device including a flow rate regulating valve is not provided, and therefore, the flow rate regulating valve in which performance is deteriorated due to contamination is not necessary, and thus, lowering reliability due to the flow rate regulating valve is not caused.

EMBODIMENTS OF THE INVENTION

Figure 1:
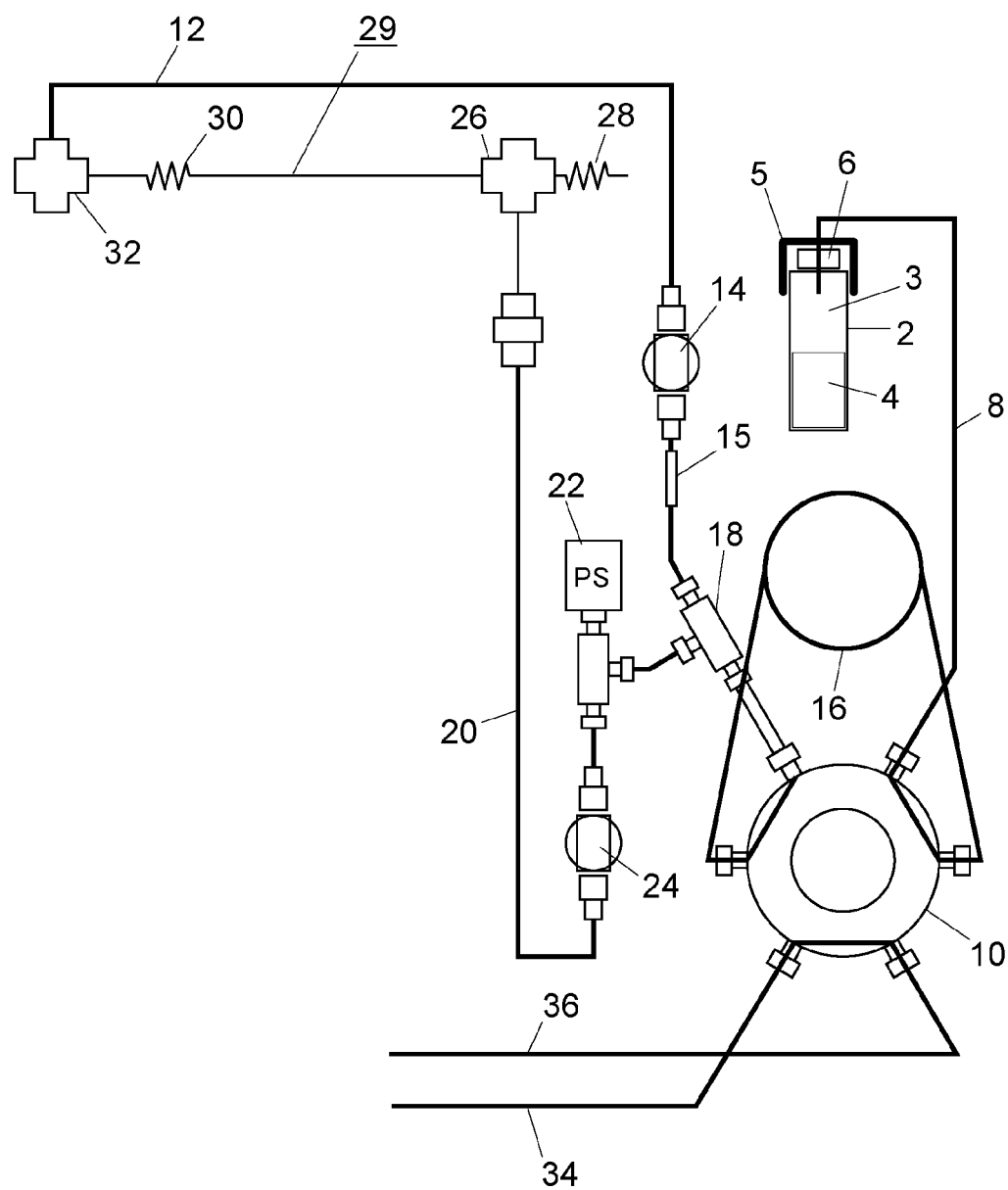
FIG. 1 is a passage diagram illustrating one embodiment of a sample introduction device.

FIG. 1 illustrates one embodiment of a sample introduction device. A sample container 2 stores therein a liquid sample or a solid sample 4, and is heated to generate a sample gas from the sample 4. The sample container 2 is sealed with a septum 6, and a space above the sample 4 in the sample container 2 is a head space 3 for storing the generated sample gas. The septum 6 is attached to the sample container 2 with a cap 5 in such a way that the inside of the sample container 2 can be pressurized to have a pressure larger than atmospheric pressure, for example, a pressure larger than atmospheric pressure by 50 to 200 kPa.

The sample container 2 is heated at a predetermined temperature for a predetermined period of time in order to generate the sample gas from the sample 4. A heating temperature is set depending on the sample gas to be measured and is, for example, 35 to 300° C. Sample components having boiling points not more than the set temperature volatilize to become the sample component gas so as to accumulate in the head space 3.

In order to collect the sample gas in the head space 3, a needle is inserted through the septum 6. The needle is provided on an end of a sample gas passage 8. A base end of the sample gas passage 8 is connected to one port of a six-way valve 10 configuring a passage switching mechanism.

A first pressurization passage 12 for applying the constant pressure larger than the atmospheric pressure in order to pressurize the inside of the sample container 2 is connected to one port of the six-way valve 10 via an on-off valve 14 configured with a solenoid valve. The on-off valve 14 also configures the passage switching mechanism. A base end of the pressurization passage 12 is connected to a pressure inlet 32. The pressure inlet 32 is a joint for pipe connection to a pressurization gas supply source.

A sample loop 16 that collects the sample gas is a passage having a predetermined capacity, and is connected to two ports of the six-way valve 10.

A discharge passage 20 is connected between the on-off valve 14 of the pressurization passage 12 and the six-way valve 10 via a T-joint 18. The discharge passage 20 has a pressure sensor (PS) 22 on an upstream side near the T-joint 18, and has an on-off valve 24 configured with a solenoid valve on a downstream side of the pressure sensor 22. The discharge passage 20 has a vent port 26 on a downstream side of the on-off valve 24. One end of a resistance pipe 28 is connected to the vent port 26, and the other end of the resistance pipe 28 is exposed to the atmosphere. Further, one end of a resistance pipe 30 is connected to the vent port 26, and the other end of the resistance pipe 30 is connected to the pressure inlet 32. The first and second resistance pipes 28, 30 configure a second pressurization passage 29 that applies a constant pressure larger than atmospheric pressure as a back pressure of the discharge passage 20 by application of a constant pressure larger than atmospheric pressure from the pressure inlet 32.

A carrier gas passage 34 to which a carrier gas is supplied and an analysis passage 36 connected to an analyzer are connected to the other two ports of the six-way valve 10.

The pressure inlet 32 is connected to the pressurization gas supply source, and the constant pressure larger than the atmospheric pressure is applied thereto from the pressurization gas supply source. The pressurization gas supply source is not limited as long as it can supply a pressurization gas having a constant pressure. The pressurization gas is an inert gas and is preferably a carrier gas used in the analyzer. An appropriate carrier gas to be used is an inert gas, such as helium, argon, or nitrogen.

Magnitude of passage resistances of the resistance pipes 28, 30 configuring the pressurization passage 29 is not limited, and a ratio between the passage resistances of the resistance pipes 28, 30 is set depending on magnitude of the pressure applied to the pressure inlet 32 and a desired back pressure to be applied to the discharge passage 20. As the resistance pipes 28, 30, for example, a pipe having an inner diameter of about 0.25 to 0.53 mm and a length of about 0.2 to 1 m is appropriate. The resistance pipes 28, 30 are not particularly limited in their materials, but for example, are stainless pipes.

As the passage resistances of the resistance pipes 28, 30 become larger, time required with the discharge passage 20 to obtain the constant back pressure becomes longer. However, gas consumption in the resistance pipes 28, 30 can be suppressed. This is advantageous in the case where the carrier gas is suitable to be used as the gas to be flown in the resistance pipes 28, 30 like this embodiment. In order to suppress the consumption of the carrier gas, the larger passage resistances of the resistance pipes 28, 30 configuring the pressurization passage 29 are advantageous.

Meanwhile, as the passage resistances of the resistance pipes 28, 30 configuring the pressurization passage 29 become smaller, the gas consumption in the pressurization passage 29 becomes larger. However, the time required with the discharge passage 20 to obtain the constant back pressure becomes shorter. This is suitable for an embodiment like an embodiment in FIG. 2, in which a gas different from the carrier gas can be used as the gas to be consumed in the pressurization passage 29.

In this embodiment, the pressurization passage 12 pressurizes the head space by supplying the inert gas to the head space from the sample gas passage 8 via the sample loop 16 with the six-way valve 10. However, the present invention is not limited to this, the pressurization passage 12 can supply the pressurization gas to the sample container 3 not via the sample loop 16.

In this embodiment, the pressurization gas supply source for the pressurization passage 12 and the pressurization gas supply source for the pressurization passage 29 are common, and thus, both the pressurization passages 12, 29 are connected to the pressure inlet 32 in common. However, the pressurization gas supply sources for both the pressurization passages 12, 29 are not necessarily common.

Figure 2:
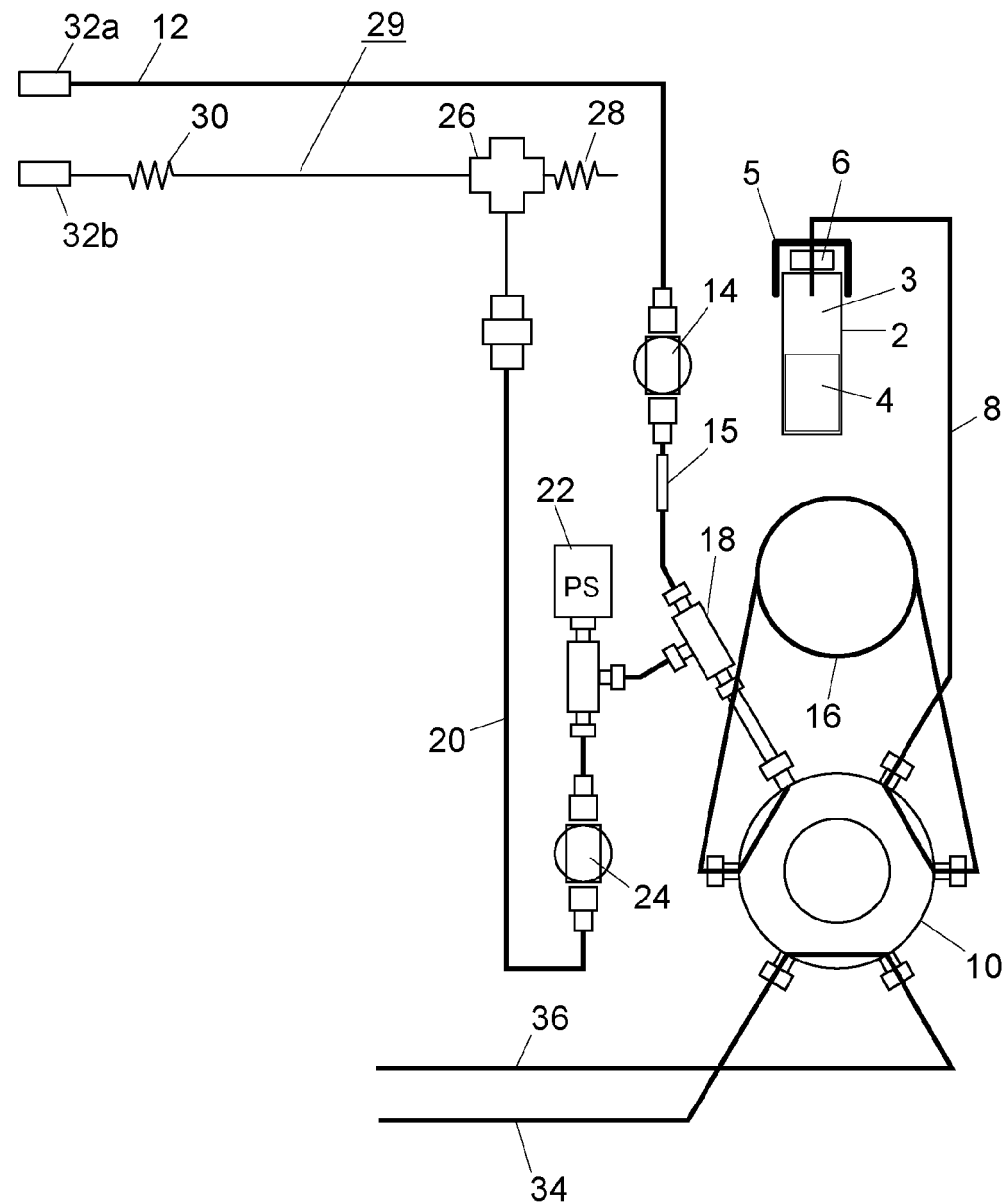
FIG. 2 is a passage diagram illustrating another embodiment of a sample introduction device.

FIG. 2 illustrates an embodiment in which a pressurization gas supply source of the pressurization passage 12 and a pressurization gas supply source of the pressurization passage 29 are different. A pressure inlet 32a is provided on the pressurization passage 12 in order to connect the pressurization passage 12 to the pressurization gas supply source, and a pressure inlet 32b different from the pressure inlet 32a is provided on the pressurization passage 29 in order to connect the pressurization passage 29 to the different pressurization gas supply source.

The pressure inlets 32a, 32b are joints for pipe connection to the respective pressurization gas supply sources. The pressure inlet 32a is connected to a carrier gas supply mechanism of an analyzer to which the sample introduction device is connected so that the carrier gas supplied to the carrier gas passage 34 as the pressurization gas is supplied as the pressurization gas. Meanwhile, the pressure inlet 32b is connected to a mechanism that pressurizes air so as to have a constant pressure larger than atmospheric pressure and supplies the air so that a gas different from the carrier gas, for example air, can be used as the pressurization gas.

Figure 3:
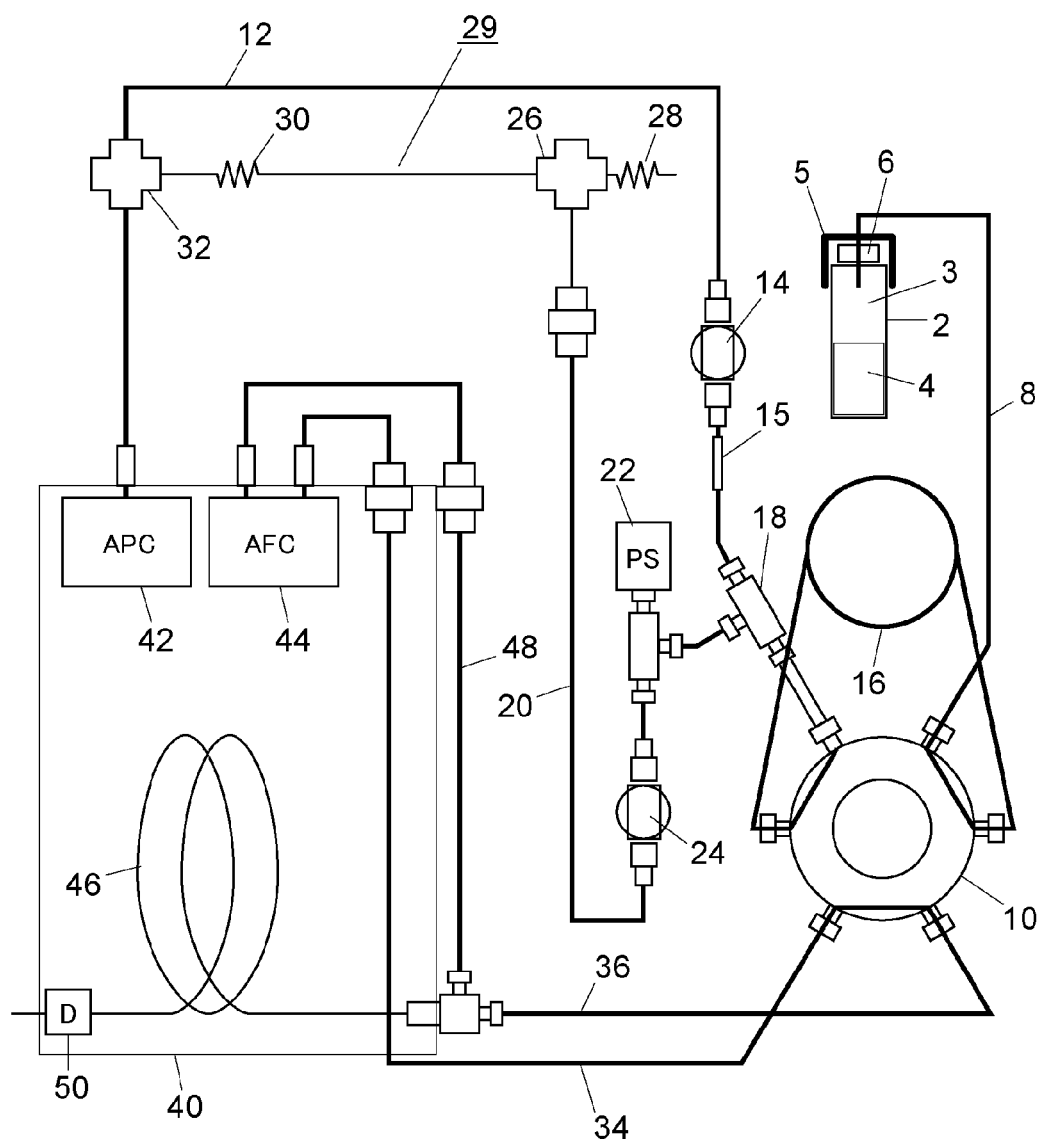
FIG. 3 is a passage diagram illustrating one embodiment of a gas chromatograph.

FIG. 3 illustrates an embodiment in which the sample introduction device in FIG. 1 is connected to a gas chromatograph main body 40 so as to configure a gas chromatograph device as a whole.

The gas chromatograph main body 40 includes a separation column 46 to which the sample gas is supplied together with the carrier gas, and a detector (D) 50 that detects sample components separated with the separation column 46. The pressure inlet 32 of the pressurization passages 12, 29 is connected to an automatic pressure control device (APC) 42 that supplies the carrier gas at a constant pressure so that the carrier gas used in the gas chromatograph is used as a pressure source of the pressurization passages 12, 29. The automatic pressure control device 42 is connected to a carrier gas supply source, such as a gas cylinder, and supplies the carrier gas adjusted to have a constant pressure larger than atmospheric pressure as the pressurization gas. When the automatic pressure control device 42 is provided on the gas chromatograph main body 40 as its attachment, the attached automatic pressure control device 42 can be used. When the automatic pressure control device 42 is not provided on the gas chromatograph main body 40 as its attachment, the automatic pressure control device 42 is separately provided.

The carrier gas passage 34 of the sample introduction device is connected to an automatic flow rate control device (AFC) 44 of the gas chromatograph main body 40, and the carrier gas adjusted to have a constant flow rate with the automatic flow rate control device 44 is supplied to the carrier gas passage 34. The analysis passage 36 of the sample introduction device is connected to the separation column 46 of the gas chromatograph. The analysis passage 36 diverges with a T-joint from an upstream side of the separation column 46 and is also connected to a split passage 48. An end of a downstream side of the split passage 48 is connected to the automatic flow rate control device 44 in order that the carrier gas split has a constant flow rate.

The same carrier gas, for example helium, is supplied from the automatic pressure control device 42 and the automatic flow rate control device 44.

Operation of the embodiment in FIG. 3 is described with reference to FIG. 4 to FIG. 6.

Figure 4:
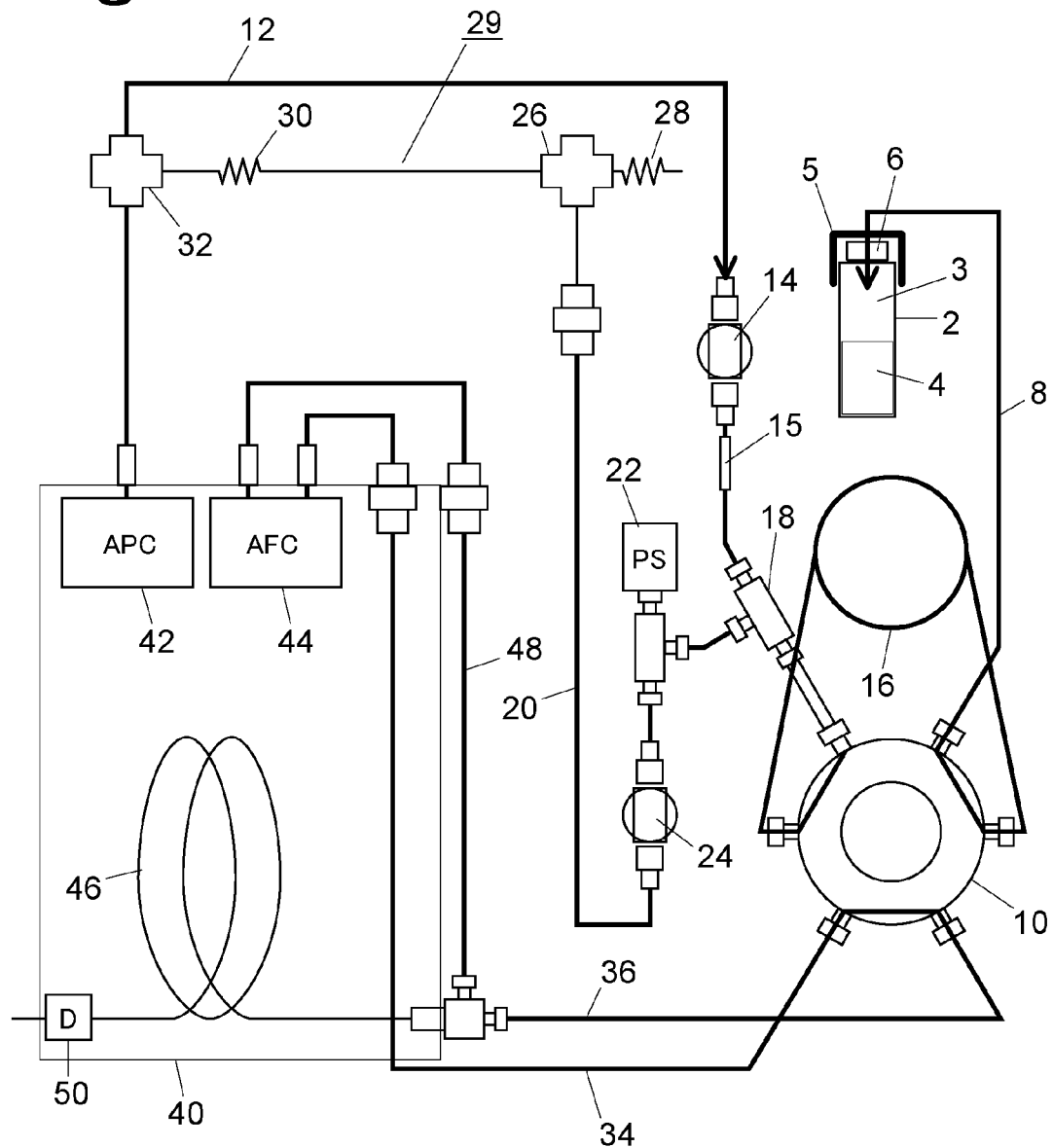
FIG. 4 is a passage diagram illustrating a step of pressurizing an inside of a sample container in the gas chromatograph of the embodiment.

FIG. 4 illustrates a step of heating the sample inside the sample container 2 to generate the volatile gas from the sample and then pressurizing the inside of the sample container 2. A liquid sample or a solid sample is put in as the sample inside the sample container 2. An upper opening of the sample container 2 is closed with the septum 6 to seal the sample container 2, and the septum 6 is secured and tightened with a cap 5. In such a state, the sample container 2 is heated at a predetermined temperature for a predetermined period of time. Thereby, the volatile gas is generated as the sample gas from the sample 4 and accumulates in the head space 3 inside the sample container 2.

In order to collect the sample gas in the head space 3, the head space 3 is pressurized until the head space 3 has the predetermined pressure larger than the atmospheric pressure. Therefore, the needle provided on the end of the sample gas passage 8 penetrates to the sample container 2 through the septum 6 of the sample container 2. The six-way valve 10 is in a state in FIG. 4, the on-off valve 24 is closed, and the on-off valve 14 is opened. Thereby, the carrier gas having the constant pressure is supplied from the pressurization passage 12 as the pressurization gas, the pressurization gas is supplied to the sample container 2 from the sample gas passage 8 via the sample loop 16, and the head space 3 has the predetermined pressure. The pressure inside the head space 3 at this time is a pressure adjusted with the automatic pressure control device 42. The pressure is detected with the pressure sensor 22.

Figure 5:
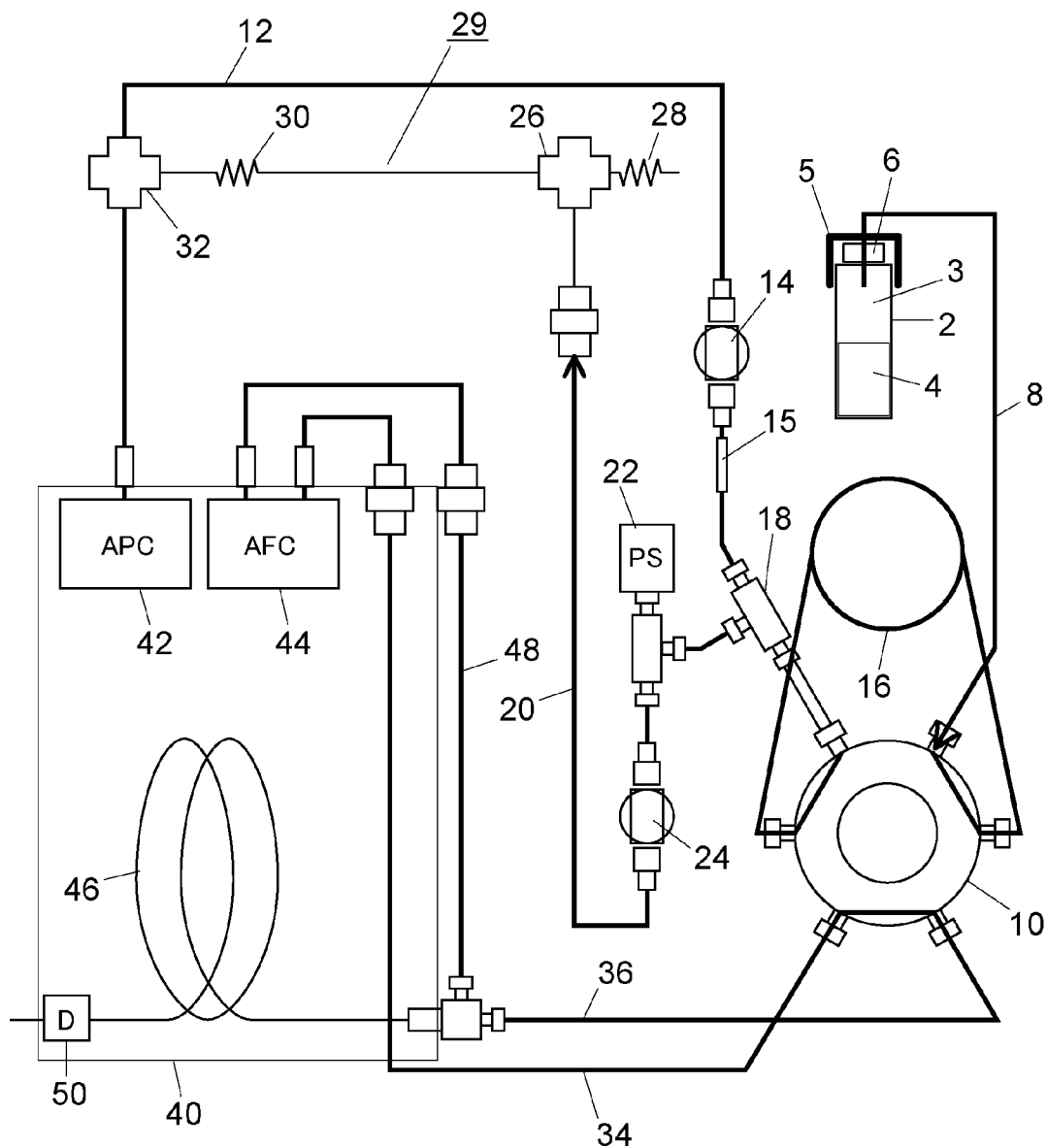
FIG. 5 is a passage diagram illustrating a sample collection step in the gas chromatograph of the embodiment.

Next, as illustrated in FIG. 5, the state of the six-way valve 10 is maintained as it is, the on-off valve 14 is closed, and the on-off valve 24 is opened. Thereby, the sample gas in the head space 3 is passed from the sample gas passage 8 to the discharge passage 20 through the sample loop 16 and then discharged from the vent port 26 through the first resistance pipe 28 into the atmosphere. At this time, the back pressure having the constant pressure larger than the atmospheric pressure is applied to the discharge passage 20 with the pressurization passage 29. The back pressure is a pressure obtained by dividing the constant pressure adjusted with the automatic pressure control device 42 with the resistance pipes 28, 30, and an initial pressure inside the sample container 2 is a pressure adjusted with the automatic pressure control device 42 itself, and thus, the back pressure of the discharge passage 20 is smaller than the initial pressure inside the sample container 2. Therefore, as illustrated with a graph A indicated by a solid line in FIG. 7, the pressure inside the sample loop 16 decreases toward the back pressure of the discharge passage 20 and eventually becomes constant at the back pressure. The pressure inside the sample loop 16 at this time is detected with the pressure sensor 22. If the resistance pipe 28 is not provided and the vent port 26 is exposed to the atmosphere, the pressure inside the sample loop 16 decreases toward the atmospheric pressure as illustrated with a graph B indicated by a broken line in FIG. 7, and eventually becomes constant at the atmospheric pressure.

In the step of discharging the sample gas inside the head space 3 through the discharge passage 20, the sample gas comes in contact with the pressure sensor 22. However, in the pressure sensor, the target gas from which the pressure is detected comes in contact with the pressure sensor, but does not pass through the inside of the sensor like a flow rate sensor, thus being less likely to cause performance deterioration due to contamination of the target gas. If the flow rate sensor is provided somewhere in the discharge passage, the flow rate sensor is contaminated with the target gas to deteriorate its performance.

Figure 6:
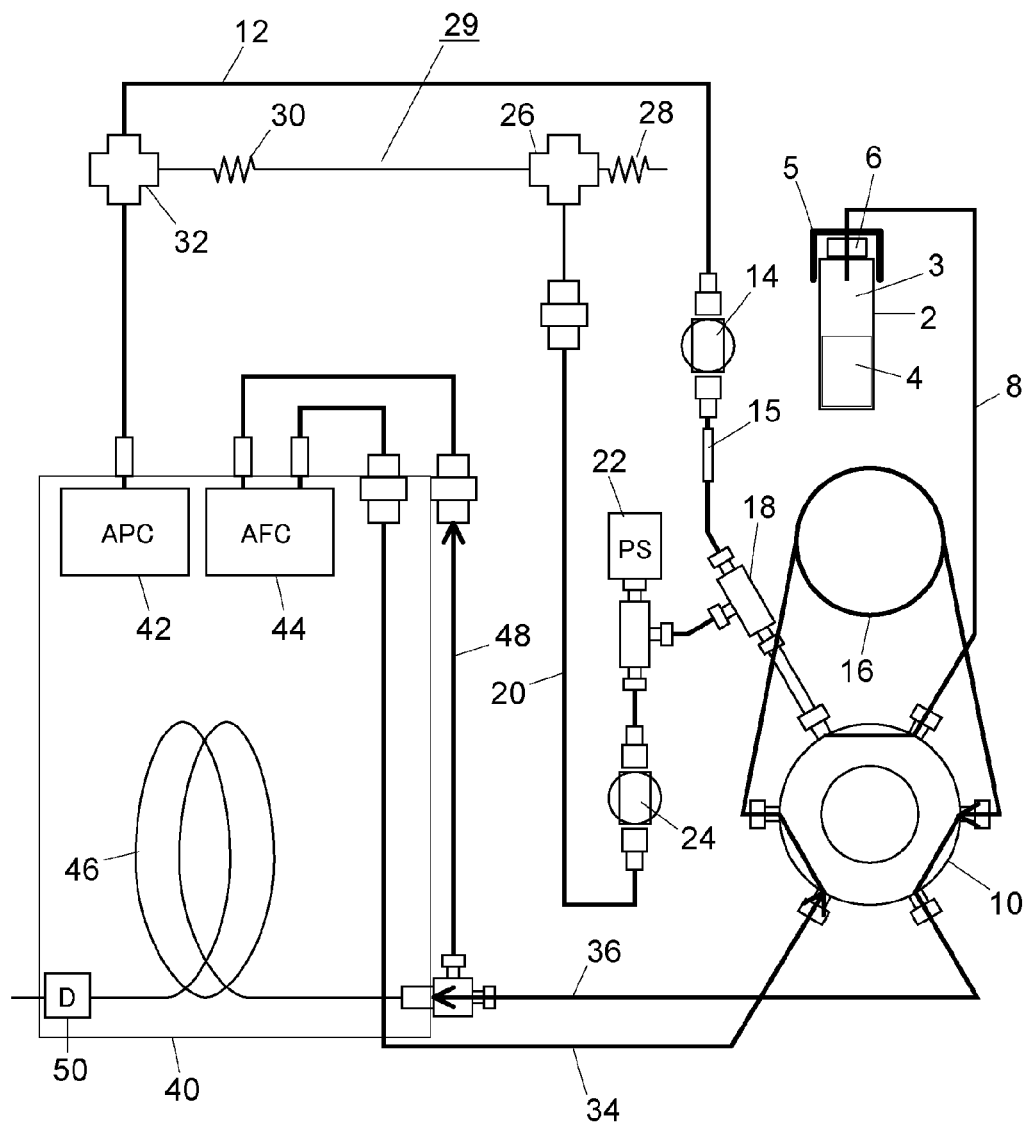
FIG. 6 is a passage diagram illustrating a sample introduction step in the gas chromatograph of the embodiment.

Next, when the pressure inside the sample loop 16 becomes constant, the sample is introduced into the gas chromatograph by switching the six-way valve 10 to a state illustrated in FIG. 6. In the sample introduction process, the carrier gas supplied from the carrier gas passage 34 passes through the sample loop 16 to push out the sample gas collected inside the sample loop 16 and sends out the sample gas from the analysis passage 36 to the gas chromatograph.

In the gas chromatograph afterward, the remaining gas split with the split passage 48 is sent into the separation column 46 and is separated into the sample components with the separation column 46. The detector 50 is provided on a downstream side of the separation column 46, and detects the sample components separated with the separation column 46.

The process of introducing the sample into the gas chromatograph is described in detail. As to the switching of the six-way valve 10 for the sample introduction, as illustrated with the graph indicated by the solid line in FIG. 7, the six-way valve 10 is switched within a time region a in which the pressure A inside the sample loop 16 is stable, and the sample gas inside the sample loop 16 is introduced into the gas chromatograph. The pressure inside the sample loop 16 is observed with the pressure sensor 22, and when a detection value of the pressure sensor 22 is stable, the six-way valve 10 is switched. The six-way valve 10 can be switched automatically with a control device of the gas chromatograph on the basis of detection output of the pressure sensor 22. Alternatively, an operator can switch the six-way valve 10 manually. Since timing a at which the six-way valve 10 is switched is a state where the pressure is stable, a concentration of the collected sample gas is stable even if the timing is slightly deviated in time. Further, since the pressure at that time is larger than the atmospheric pressure, the sample gas concentration is higher than that in the case where the sample is collected in the atmospheric pressure state, and thus a highly sensitive analysis can be performed.

Figure 7:
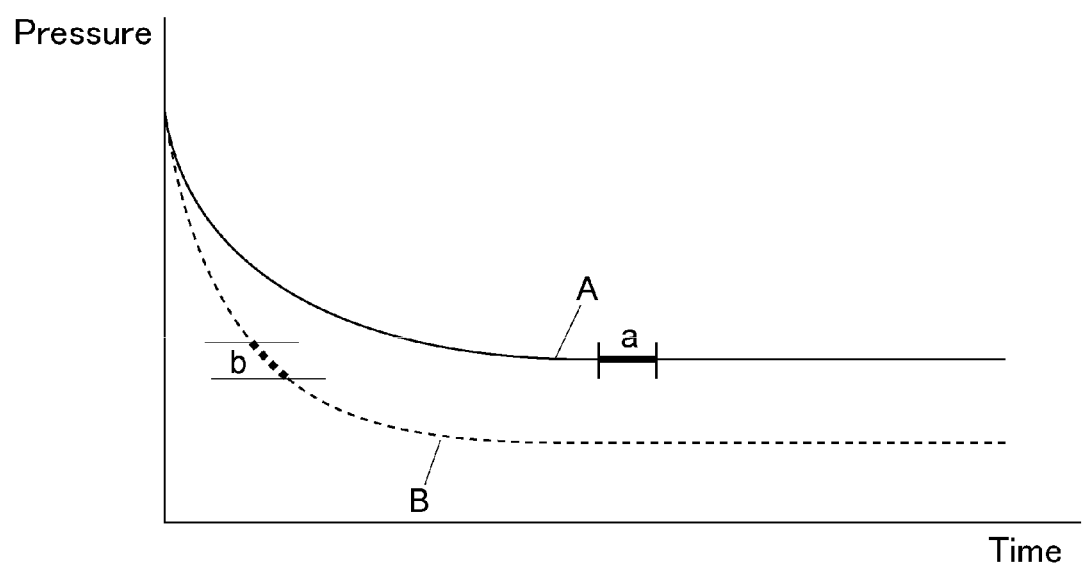
FIG. 7 is a graph illustrating change of a detected pressure with time with a pressure sensor in the sample collection step in the gas chromatograph of the embodiment.

Meanwhile, in the case where the pressurization passage 29 is not provided, as illustrated with the graph B indicated by the broken line in FIG. 7, if the sample gas is collected when the pressure becomes constant, the sample gas is collected in the atmospheric pressure state. Therefore, if the six-way valve 10 is switched when the pressure is the same as that in this embodiment, the six-way valve 10 needs to be switched at timing illustrated with b. Since the timing b is timing during which the pressure inside the sample loop 16 decreases, if the timing at which the six-way valve 10 is switched is deviated, the concentration of the collected sample gas fluctuates, thus, lowering reproducibility of a measuring result.

Figure 8:
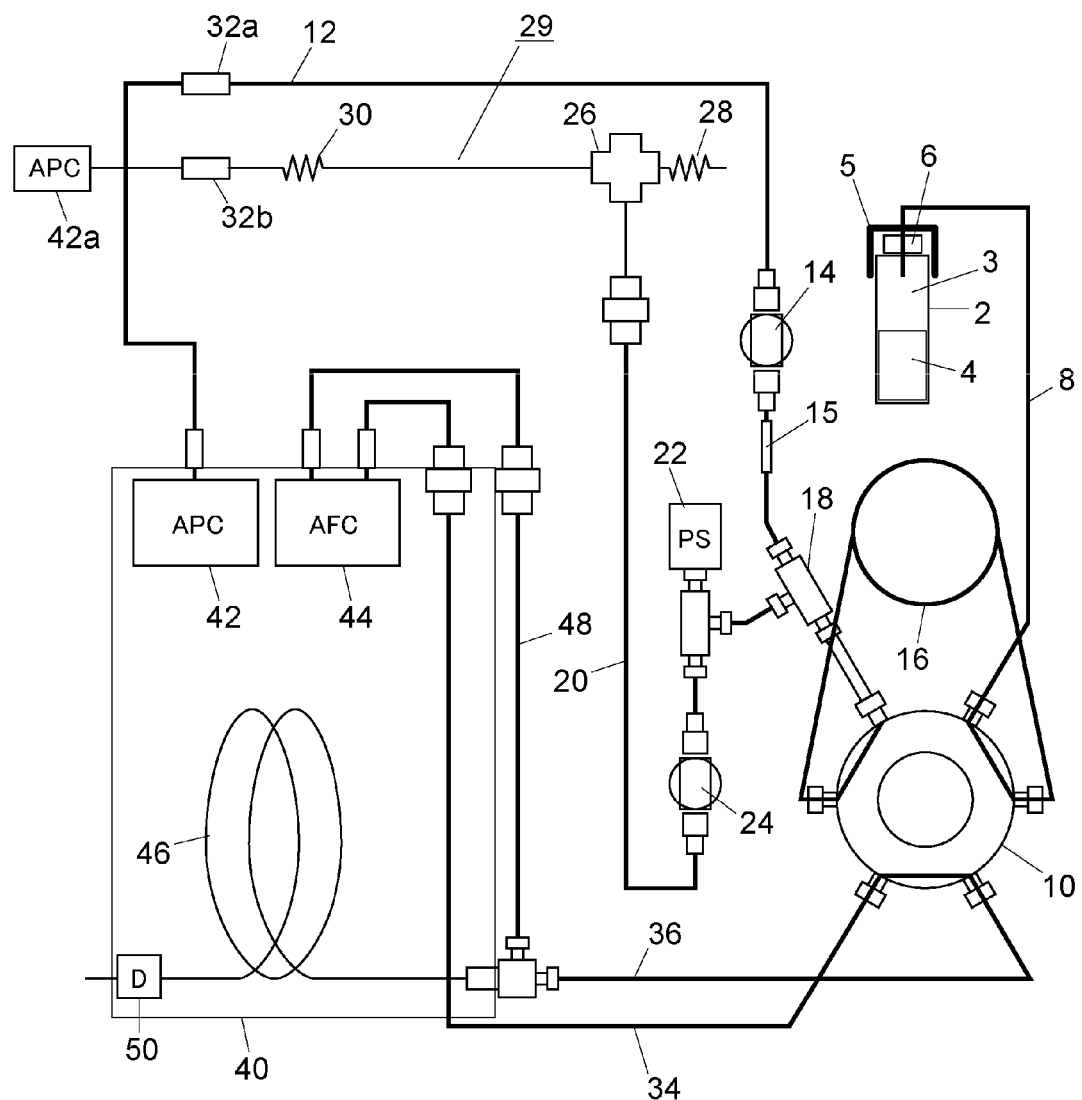
FIG. 8 is a passage diagram illustrating a gas chromatograph using the sample introduction device in FIG. 2.

FIG. 8 illustrates an embodiment of a gas chromatograph using the sample introduction device in FIG. 2.

A gas chromatograph main body 40 is the same as that illustrated in the embodiment in FIG. 3. The pressure inlet 32a of the pressurization passage 12 is connected to the automatic pressure control device 42 that supplies the carrier gas at the constant pressure so that the carrier gas used in the gas chromatograph is used as the pressure source of the pressurization passage 12.

Meanwhile, the pressure inlet 32b of the pressurization passage 29 for applying the back pressure of the discharge passage 20 is connected to an automatic pressure control device 42*a* different from the automatic pressure control device 42. The automatic pressure control device 42*a* can supply an optional gas as the pressurization gas. It is preferable that the automatic pressure control device 42*a* uses a gas cheaper than the gas used as the carrier gas in the gas chromatograph, such as air, or nitrogen. Since the other configurations are the same as those of the embodiment in FIG. 3, description thereof is omitted. Since operation is the same as that of the embodiment in FIG. 3, description thereof is also omitted.

DESCRIPTION OF REFERENCE SIGNS 2 sample container
3 head space
8 sample gas passage
10 six-way valve
12 first pressurization passage
14, 24 on-off valve
16 sample loop
20 discharge passage
28, 30 resistance pipe
29 second pressurization passage
34 carrier gas passage
36 analysis passage
40 gas chromatograph main body
46 separation column
50 detector

The invention claimed is:

1. A head space sample introduction device comprising:
a sample gas passage connected to a head space of a sample container, the head space for storing a sample gas generated from a sample;
a first pressurization passage connecting to a pressurization gas supply source of a constant first pressure larger than atmospheric pressure;
a sample loop for holding the sample gas;
a discharge passage for discharging the sample gas;
a carrier gas passage for supplying a carrier gas;
an analysis passage connected to an analyzer;
a passage switching mechanism for switching among (1) a head space pressurization passage configuration in which the first pressurization passage is connected to the head space, (2) a sample gas collection passage configuration in which the sample loop is connected between the sample gas passage and the discharge passage, and (3) a sample gas introduction passage configuration in which the sample loop is connected between the carrier gas passage and the analysis passage; and
a second pressurization passage including:

a first resistance pipe having one end connected to a downstream side of the discharge passage and the other end exposed to the atmosphere; and
a second resistance pipe having one end connected to the downstream side of the discharge passage and the other end connected to a pressurization gas supply source of a constant second pressure larger than atmospheric pressure,
the second pressurization passage a applying to the discharge passage a constant pressure larger than atmospheric pressure obtained by passing the second pressure through the first and second resistance pipes.

2. The head space sample introduction device according to claim 1, wherein the pressurization gas supply source to which the first pressurization passage is connected, and the pressurization gas supply source to which the second pressurization passage is connected are common to each other.

3. The head space sample introduction device according to claim 1, wherein the pressurization gas supply source to which the first pressurization passage is connected, and the pressurization gas supply source to which the second pressurization passage is connected are different from each other.

4. A gas chromatograph comprising:
a gas chromatograph main body including a separation column to which the sample gas is supplied together with the carrier gas, and a detector for detecting a sample component separated with the separation column; and
the head space sample introduction device as described in claim 1, wherein
the analysis passage is connected to the separation column of the gas chromatograph main body as the analyzer.

5. The gas chromatograph according to claim 4, wherein the pressurization gas supply source to which the first pressurization passage is connected is configured to supply a gas identical with the carrier gas supplied from the carrier gas passage as a pressurization gas.

6. The gas chromatograph according to claim 5, wherein the pressurization gas supply source to which the first pressurization passage is connected, and the pressurization gas supply source to which the second pressurization passage is connected are common to each other.

7. The gas chromatograph according to claim 5, wherein the pressurization gas supply source to which the first pressurization passage is connected, and the pressurization gas supply source to which the second pressurization passage is connected are different from each other.

8. The head space sample introduction device according to claim 1, wherein the pressurization gas supply source to which the first pressurization passage is connected is configured to supply a gas identical with the carrier gas supplied from the carrier gas passage as a pressurization gas.

* * * * *